(12) United States Patent
Kang et al.

(10) Patent No.: US 6,946,294 B2
(45) Date of Patent: Sep. 20, 2005

(54) TRANSGENIC PLANT TRANSFORMED WITH A TRANSLATIONALLY CONTROLLED TUMOR PROTEIN (TCTP) GENE

(75) Inventors: Jeong-Gu Kang, Kwangju (KR); Ju Yun, Kwangju (KR); Pill-Soon Song, Kwangju (KR); Chung-Mo Park, Kwangju (KR)

(73) Assignee: Kumho Petrochemical Co., Seoul (KR)

( * ) Notice: Subject to any disclaimer, the term of this patent is extended or adjusted under 35 U.S.C. 154(b) by 0 days.

(21) Appl. No.: 10/345,599

(22) Filed: Jan. 16, 2003

(65) Prior Publication Data

US 2003/0131384 A1 Jul. 10, 2003

Related U.S. Application Data

(62) Division of application No. 09/737,300, filed on Dec. 15, 2000, now Pat. No. 6,545,202.

(30) Foreign Application Priority Data

Sep. 22, 2000 (KR) .................................... 2000-0055727

(51) Int. Cl.$^7$ ............................ C12N 5/10; C12N 15/82
(52) U.S. Cl. .................................... 435/419; 435/320.1
(58) Field of Search ................................ 800/290, 298, 800/278; 536/24.5, 23.6; 435/320.1, 468, 419

(56) References Cited

U.S. PATENT DOCUMENTS 6,545,202 B2 * 4/2003 Kang et al. .............. 800/317.3

OTHER PUBLICATIONS

Kang et al., NCBI Accession No. AF107842, Jul. 2, 1999.*

Maniatis et al., Molecular Cloning A Laboratory Manual, 1982, Cold Spring Harbor Laboratory, New York, pp. 404–421.*

Yuval Eshed, et al., Establishment of polarity in lateral organs of plants, Current Biology, vol. 11, No. 16, pp. 1251–1260.

Kimiyo Sage–Ono, et al., Dark–Induced Accumulation of mRNA for a Homolog of Translationally Controlled Tumor Protein (TCTP) in Pharbitis, Plant Cell Physiology, 39(3): (1998), pp. 357–360.

Jean Finnegan and David McElroy, Transgene Inactivation: Plants Fight Backl. Bio/Technology vol. 12, Sep. 1994, pp. 883–887.

* cited by examiner

*Primary Examiner*—Ashwin Mehta
(74) *Attorney, Agent, or Firm*—Matthews, Shepherd, McKay & Bruneau, P.A.

(57) ABSTRACT

The present invention provides transgenic higher plants and transgenic plant cells thereof which have been transformed with a plant translationally controlled tumor protein (TCTP) gene to improve growth rate in a growth stage-dependent manner, especially in the earlier vegetative growth stage from seedlings to young plants. Also, the invention provides methods for engineering higher plants so that they can be more efficiently transformed with other transforming vector constructs. Further, provided are TCTP expression vectors which contain an uninterrupted coding region for the TCTP protein used to generate transgenic plants and cells thereof.

4 Claims, 7 Drawing Sheets

```
1    ATGTTGGTTTACCAGGATCTTCTCTCCGGTGATGAGCTCCCTTCGGATTCATTTTCCTAC
1     M   L   V   Y   Q   D   L   L   S   G   D   E   L   P   S   D   S   F   S   Y

61   ACTGAACTTGGGAATGGAGTGCTTTGGGAAGTGCAAGGGAAGTGGGTTGTTCAGGGAGCT
21    T   E   L   G   N   G   V   L   W   E   V   Q   G   K   W   V   V   Q   G   A

121  GTTGATGTGAACATCGGGGCGAATCCATCTGCTGAAGGTGCAGATGAAGACGAAGGTGTT
41    V   D   V   N   I   G   A   N   P   S   A   E   G   A   D   E   D   E   G   V

181  GACGATCAAGCCATCAAGGTTGTCGATATTGTTGACACTTTCAGGCTTCAGGAGCAACCT
61    D   D   Q   A   I   K   V   V   D   I   V   D   T   F   R   L   Q   E   Q   P

241  TCTTTTGACAAGAAGCAGTTTGTTGCCTACATGAAGAAATATATCAAGAACCTAACACCC
81    S   F   D   K   K   Q   F   V   A   Y   M   K   K   Y   I   K   N   L   T   P

301  AAGTTAGGCGCAGAGCAGGAAGAAGTTTTTAAGAACAACATTCAAGGAGCAACCAAGTAC
101   K   L   G   A   E   Q   E   E   V   F   K   N   N   I   Q   G   A   T   K   Y

361  CTTTTGTCAAAGCTCAGTGACCTTCAATTCTTTGTTGGTGAGAGCATGGCTGATGATACT
121   L   L   S   K   L   S   D   L   Q   F   F   V   G   E   S   M   A   D   D   T

421  GGAATGGTGTTTGCCTACTACAAGGATGGCGCCACTGATCCTACCTTTTTGTACCTCGCA
141   G   M   V   F   A   Y   Y   K   D   G   A   T   D   P   T   F   L   Y   L   A

481  CATGGACTCAAGGAGGTCAAGTGTTAA
161   H   G   L   K   E   V   K   C   *
```

```
            1               15 16          30 31              45 46                60 61              75 76           90
            M----D----DE--S D-------------E ---------------G-- ----I--N--S----- ------------------ ---------V-- -V----------
Alfalfa     MLVYQDLLTGDELLS DSYPYKEIENGMLWE VEGKWVTK--GV--V E-VDIGANASA-EGG EDEGVDDTAVKVV-D IVDVFR-LQEQPAFD 82
Pea         MLVYQDLLTGDELLS DSYPYKEIENGMLWE VEGKWVVK--GA--V D-VNIGANPSA-EGG EDEGVDDTAVKVV-D IVDVFR-LQEQPPFD 82
Arabidopsis MLVYQDLLTGDELLS DSFPYKEIENGILWE VEGKWVTV--GA--V D-VNIGANPSAEGGG EDEGVDDSAQKVV-D IVDTFR-LQEQPTYD 83
Pine        MIVYQDLLSGDELLS DSFPYKELNNGVLWE VEGKWLSQ--GA--V D-VDIGANPSA-EGG EDEGVDDQAAKVV-D IVDTFR-LQEQPSFD 82
Potato      MLVYQDLLTGDELLS DSFPYTEIQNGMLWE VHGKWVVH--GA--V D-VNIGANPSAEGGG EDEGVDDQAVKVV-D IVDTFR-LQEQPAFD 83
Rice        MLVYQDLLTGDELLS DSFPYREIENGILWE VDGKWVVQ--GA--I D-VDIGANPSAEGGG DDEGVDDQAVKVV-D IVDTFR-LQEQPPFD 83
Tobacco     MLVYQDLLSGDELPS DSFSYTELGNGVLWE VQGKWVVQ--GA--V D-VNIGANPSAEGAD EDEGVDDQAIKVV-D IVDTFR-LQEQPSFD 83
Pharbitis   MLVYQDLLTGDELLS DSFCYKEIESGVLWE VEGKWVVQ--GA--V D-VDIGANPSADGAD EDEGVDDKAVKVV-D IVDHFQTSTEQPPFD 84

91              105 106         120 121             135 136              150 151             165 166           180
            K-------K---K-- ---L------E---F ---------------- ---------F--GE--M---D- ----------------- ----------P----K-
Alfalfa     KKQFLGFVKRYIKLL TPKL---DAEKQELF KKHIEGATKYLLCKL KDLQFFVGESMHDDG SLVFAYY-KDGAADP TFLYFAYALKEIKC 167
Pea         KKQFLGFVKKYIKLL TPKL---EAEKQEHF KKNIEGATKYLLGKL KDLQFFVGESMHDDG SLVFAYY-KDGAADP TFLYFSFALKEIKC 167
Arabidopsis KKQFIAYIKKYIKLL TPKL---SEEDQAVF KKGIEGATKFLLPRL SDFQFFVGEGMHDDS TLVFAYY-KEGSTNP TFLYFAHGLKEVKC 168
Pine        KKQFLAFIKRYIKNL ATKL---SEERQAEF KKNVEAAAKWLVSKL SDLQFFVGEGMHDDS SMVFAYY-KEGATDP TFLYFADGLKEVKC 167
Potato      KKQFVTYIKRYIKSL TPKL---EGEAQEAF KENIESATKFLLSKL KDFQFFVGEGMHDDS ALVFAYY-KDGSADP TFLYLAPGLKEIKC 168
Rice        KKQFVTFMKRYIKNL SAKL---DAEKQEEF KKNIEGATKYLLGKL KDLQFFVGESMHDDG GLVFAYY-KDGATDP TFLYFSHGLKEVKC 168
Tobacco     KKQFVAYMKKYIKNL TPKL---GAEQEEVF KNNIQGATKYLLSKL SDLQFFVGESMADDT GMAFAYY-KDGATDP TFLYLAHGLKEVKC 168
Pharbitis   KKQFVAYIKKYIKLL TPKL---DAEKQEVF KKNIEGEPSSCSQSL -VPEFFVGESMSDDS TLVFAYY-KDGASDP TFLYFAHGLKEVKC 168

Human       KEAYKKYIKDYMKSI KGKLEEQRPERVKPF MTGAAEQIKHILANF KNYQFFIGENMNPDG MVALLDYREDGVT-P YMIFFKDGLEMEKC 172
Mouse       KEAYKKYIKDYMKSL KGKLEEQKPERVKPF MTGAABQIKHILANF NNYQFFIGENMNPDG MVALLDYREDGVT-P FMIFFKDGLEMEKC 172
Rabbit      KEAYKKYIKDYMKSI KGKLEEQRPERVKPF MTGAAEQIKHILANL KNYQFFIGENMNPDG MVALLDYREDGVT-P FMIFFKDGLEMEKC 172
Chicken     KESYKKYIKDYMKAI KARLEEHKPERVKPF MTGAAEQIKHILANF KNYQFFVGENMNPDG MVALLDFREDGVT-P YMIFFKDGLEIEKC 172

F.yeast     KESYMSYIKGYMKAI KARLQESNPERVPVF EKNAIGFVKKILANF KDYDFYIGESMDPDA MVVLMNYREDGIT-P YMIFFKDGLVSEKF 168
Yeast       KKSFLTYIKGYMKAV KAKLQETNPEEVPKF EKGAQTVKKVIGSF KDWEFFTGESMDPDA MVVMLNYREDGTT-P FVAIWKGIVEEKI 167
```

MIIYRDLISHDEMFS DIYKIREIADGLCLE VEGKMVSRTEGN--I DDSLIGGNASA-EGP EGEGTESTVITGV-D IVMNHH-LQE-TSFT 84
                                                                        MIIYRDLISHDELFS DIYKIREIADGLCLE VEGKMVSRTEGA--I DDSLIGGNASA-EGA EGEGTESTVVIGV-D IVMNHH-LQE-TSFT 84
                                                                        MIIDRDLISHDETFS DIYKIREIAGGLCLE VEGKMVSRTEGN--I DDSLIGGNASA-EGP EGEGTESTVITGV-D IVMNHH-LQE-TSFT 84
                                                                        MIIYRDCISQDEMFS DIYKIREVANGLCLE VEGKMVTRTEGQ--I DDSLIGGNASA-EGP EGEGTEATVITGV-D IVINHH-LQE-TSFT 84

MLLYKDVISGDELVS DAYDLKEV-DDIVYE ADCQMVTVKQGD-V D----IGANPSA-EDA EENAEEGT--ETVNN LVYSFR-LSE-TSFT 80
                                                                        MIIYKDIFSNDELLS DAYDAKLV-DDVIYE ADCAMVNV--GGDNI D----IGANPSA-EGG DDDVEEGA--EMVNN VVHSFR-LQ-QTAFD 79

Day-12

S  AS  C

Day-40

S  AS  pBI121

FIG. 9

SEQUENCE LISTING

```
<160> NUMBER OF SEQ ID NOS: 9

<210> SEQ ID NO 1
<211> LENGTH: 507
<212> TYPE: DNA
<213> ORGANISM: Nicotiana tabacum
<220> FEATURE:
<221> NAME/KEY: CDS
<222> LOCATION: (1)..(504)
<220> FEATURE:
<223> OTHER INFORMATION: DNA encoding ntTCTP protein

<400> SEQUENCE: 1 atg ttg gtt tac cag gat ctt ctc tcc ggt gat gag ctc cct tcg gat      48
Met Leu Val Tyr Gln Asp Leu Leu Ser Gly Asp Glu Leu Pro Ser Asp
  1               5                  10                  15 tca ttt tcc tac act gaa ctt ggg aat gga gtg ctt tgg gaa gtg caa      96
Ser Phe Ser Tyr Thr Glu Leu Gly Asn Gly Val Leu Trp Glu Val Gln
             20                  25                  30 ggg aag tgg gtt gtt cag gga gct gtt gat gtg aac atc ggg gcg aat     144
Gly Lys Trp Val Val Gln Gly Ala Val Asp Val Asn Ile Gly Ala Asn
         35                  40                  45 cca tct gct gaa ggt gca gat gaa gac gaa ggt gtt gac gat caa gcc     192
Pro Ser Ala Glu Gly Ala Asp Glu Asp Glu Gly Val Asp Asp Gln Ala
     50                  55                  60 atc aag gtt gtc gat att gtt gac act ttc agg ctt cag gag caa cct     240
Ile Lys Val Val Asp Ile Val Asp Thr Phe Arg Leu Gln Glu Gln Pro
 65                  70                  75                  80 tct ttt gac aag aag cag ttt gtt gcc tac atg aag aaa tat atc aag     288
Ser Phe Asp Lys Lys Gln Phe Val Ala Tyr Met Lys Lys Tyr Ile Lys
                 85                  90                  95 aac cta aca ccc aag tta ggc gca gag cag gaa gaa gtt ttt aag aac     336
Asn Leu Thr Pro Lys Leu Gly Ala Glu Gln Glu Glu Val Phe Lys Asn
            100                 105                 110
```

```
aac att caa gga gca acc aag tac ctt ttg tca aag ctc agt gac ctt    384
Asn Ile Gln Gly Ala Thr Lys Tyr Leu Leu Ser Lys Leu Ser Asp Leu
            115                 120                 125 caa ttc ttt gtt ggt gag agc atg gct gat gat act gga atg gtg ttt    432
Gln Phe Phe Val Gly Glu Ser Met Ala Asp Asp Thr Gly Met Val Phe
130                 135                 140 gcc tac tac aag gat ggc gcc act gat cct acc ttt ttg tac ctc gca    480
Ala Tyr Tyr Lys Asp Gly Ala Thr Asp Pro Thr Phe Leu Tyr Leu Ala
145                 150                 155                 160 cat gga ctc aag gag gtc aag tgt taa                                507
His Gly Leu Lys Glu Val Lys Cys
                165
```

<210> SEQ ID NO 2
<211> LENGTH: 168
<212> TYPE: PRT
<213> ORGANISM: Nicotiana tabacum
<220> FEATURE:
<223> OTHER INFORMATION: ntTCTP protein

<400> SEQUENCE: 2

```
Met Leu Val Tyr Gln Asp Leu Leu Ser Gly Asp Glu Leu Pro Ser Asp
 1               5                  10                  15

Ser Phe Ser Tyr Thr Glu Leu Gly Asn Gly Val Leu Trp Glu Val Gln
            20                  25                  30

Gly Lys Trp Val Val Gln Gly Ala Val Asp Val Asn Ile Gly Ala Asn
        35                  40                  45

Pro Ser Ala Glu Gly Ala Asp Glu Asp Glu Gly Val Asp Asp Gln Ala
    50                  55                  60

Ile Lys Val Val Asp Ile Val Asp Thr Phe Arg Leu Gln Glu Gln Pro
65                  70                  75                  80

Ser Phe Asp Lys Lys Gln Phe Val Ala Tyr Met Lys Lys Tyr Ile Lys
                85                  90                  95

Asn Leu Thr Pro Lys Leu Gly Ala Glu Gln Glu Val Phe Lys Asn
            100                 105                 110

Asn Ile Gln Gly Ala Thr Lys Tyr Leu Leu Ser Lys Leu Ser Asp Leu
        115                 120                 125

Gln Phe Phe Val Gly Glu Ser Met Ala Asp Asp Thr Gly Met Val Phe
130                 135                 140

Ala Tyr Tyr Lys Asp Gly Ala Thr Asp Pro Thr Phe Leu Tyr Leu Ala
145                 150                 155                 160

His Gly Leu Lys Glu Val Lys Cys
                165
```

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic Primer

<400> SEQUENCE: 3
cgcggatcca tgttggttta tcaggat                                       27

<210> SEQ ID NO 4
<211> LENGTH: 27
<212> TYPE: DNA
<213> ORGANISM: Artificial Sequence

```
<220> FEATURE:
<223> OTHER INFORMATION: Description of Artificial Sequence: Synthetic
      Primer

<400> SEQUENCE: 4
ctcgtcgaca cacttgacct ccttgag                                          27

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
ccgccgtggg gaaagcacag atactagcta                                       30

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
ctagctagta tctgtgcttt ccccacggcg g                                     31

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
ctgggatacc gctggtctag aacgatatag agca                                  34

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
ctgctctata tcgttctaga ccagcggtat cccag                                 35

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
ctcgtcgacg cacttgatct ccttcaaag                                        29
```

TRANSGENIC PLANT TRANSFORMED WITH A TRANSLATIONALLY CONTROLLED TUMOR PROTEIN (TCTP) GENE

This application is a divisional of U.S. Ser. No. 09/737,300, filed on Dec. 15, 2000, now U.S. Pat. No. 6,545,202.

BACKGROUND OF THE INVENTION

1. Technical Field of the Invention

The present invention relates to transgenic higher plants and transgenic plant cells thereof wherein the transgenic plant cells have been transformed with a gene encoding the translationally controlled tumor protein (TCTP). The transgenic higher plants grow about 30% faster than the parental plants during the juvenile growth stage.

The present invention relates to a method to engineer higher plants that can be more readily infected with *Agrobacterial* cells and from which more calli are induced in tissue cultures than the parental plants.

2. Description of the Prior Art

Plant growth and development are regulated by complex interactions between various environmental factors and endogenous developmental programs, such as plant growth hormones. Since plants are sessile, they have developed sophisticated systems to adapt themselves and to optimize their growth and development in response to ambient environmental conditions. Light is one of the most important environmental factors in that it is not only the sole energy source for plant growth but also regulates a variety of plant photomorphogenic responses, from seed germination to floral development (Kendrick et al. 1994). Plants therefore possess specialized photoreceptor proteins to precisely perceive light signals in the forms of wavelength, intensity, direction, and duration. Several photoreceptors that fulfil distinct physiological roles have been characterized so far. These include the red and far-red light absorbing phytochromes (Botto et al. 1996; Chory et al. 1996), the blue light absorbing cryptochromes (Ahmad et al. 1998; Christie et al. 1998; Cashmore et al. 1997), and the UV light absorbing UVA/B photoreceptors (Christie et al. 1996). Among them, the phytochromes are the best characterized. Phytochromes are molecular light switches that interconvert between two spectrally different forms, a photosensory red light absorbing Pr and a photoregulatory far-red light absorbing Pfr forms (Braslavsky et al. 1997; Song et al. 1996; Terry et al. 1995). Light signals perceived by phytochromes are subsequently transmitted through a series of downstream signaling components, such as G-proteins, $Ca^{2+}$/calmodulin, protein kinase/phosphatase, cAMP/cGMP, and phytohormones and finally regulate genes involved in plant photomorphogenic responses (Neuhaus et al. 1997; Wu et al. 1997; Bowler et al. 1994a; Bowler et al. 1994b).

One primary role for the phytochrome photoreceptors is the regulation of plant growth and developmental process in earlier vegetative growth stage, such as stem and leaf growth, chlorophyll biosynthesis, and shade avoidance. However, plants in this growth stage are very vulnerable to environmental and pathogenic damages, mainly due to weak stems and leaves. This could result in a great economic loss, especially when agronomic plants are densely grown.

Although the molecular signaling pathway from light perception by the photoreceptors to physiological changes at cellular levels is largely unknown, many genes involved in this signaling pathway have been isolated and molecular biologically characterized. The translationally controlled tumor protein (TCTP) is one of the recently identified growth-related proteins in plants. The TCTP protein is a highly conserved cytosolic protein among various organisms, including man, animals, plants, and yeast (Woo et al. 1997). The TCTP proteins have been originally isolated from cancerous tissues in animals and from callus tissue and rapidly growing plant parts, such as apical stems and leaves, in plant, suggesting a regulatory role in cell proliferation (Woo et al. 1997; MacDonald et al. 1995; Hughes et al. 1993). However it has been later observed that it is also expressed in healthy animal tissues and that the expression is regulated by calcium ion at both the transcriptional and post-transcriptional levels (Wu et al. 1999; Sanchez. et al. 1997). In accordance with this, it is notable that the TCTP has a $Ca^{2+}$ binding activity (Sanchez et al. 1997). The TCTP protein is colocalized with the cytoskeletal microtubular networks (Gachet et al. 1999; Gachet et al. 1997) via association with α- and β-tubulins. It is interesting that the TCTP, which is otherwise a very acidic protein, has a basic domain of about 50 amino acids in the C-terminal region, which physically interacts with the tubulins (Gachet et al. 1999). Taken together, these observations suggest that the TCTP proteins have a housekeeping role in the regulation of cell growth and differentiation.

The TCTP genes have been isolated from several plants (Sage-Ono et al. 1998; Tamaoki et al. 1997; Woo et al. 1997). However, only the sequences of genes and gene fragments have been deposited in the databases without detailed molecular biological and functional analysis except for a few cases. The pea TCTP gene is actively expressed in rapidly dividing cells within root caps (Woo et al. 1997). In a short-day plant Japanese morning glory (*Pharbitis nil* cv. Violet), the TCTP mRNA accumulates to a high level when grown in the dark, but the expression level decreases to an undetectable level in the light (Sage-Ono et al. 1998).

To investigate the physiological role(s) of the TCTP in plant growth and development, we isolated a TCTP gene homolog from *Nicotiana tabacum*. The tobacco TCTP (referred to as ntTCTP in this work) protein physically interacts with the Pra3 small GTPase, a Rab-like GTPase originally isolated from *Pisum sativum* (Yoshida et al. 1993; Nagano et al. 1995). The ntTCTP-Pra3 interaction is GTP-dependent. The ntTCTP associates exclusively with the, constitutively active GTP-bound Pra3, but not with the dominant negative GDP-bound Pra3. The ntTCTP gene is expressed in all tested plant organs, such as leaf, stem, root, and floral organs. Light does not exhibit any significant effects on the ntTCTP transcription, unlike that observed in the Japanese morning glory plant.

Transgenic higher plants of this invention grow much faster than the parental plants during the vegetative growth stage. They reach the adult stage in a shorter time (about 30% faster) and therefore potentially have less chance to be damaged by environmental factors compared to the parental plants. In addition, the transgenic plants are more rapidly regenerated and induce more calli from *Agrobacterial* infection in tissue cultures. Interestingly, transgenic plants with the pra3 small GTPase gene also showed essentially identical phenotypes as those with the ntTCTP gene, further supporting the specific Pra3-ntTCTP interaction.

With recent technical advances in plant tissue culture and gene manipulation, it is now a routine experimental technique to introduce a new gene into desired plants with an aim to improve productivity and quality. For example, vegetables can be engineered so that they grow faster or slower than the parental plants without affecting any other phenotypes. According to the present invention, the TCTP gene could be a good tool for the genetic manipulation of plant growth rate.

As used herein, the term "higher plants" refers to multicellular differentiated organisms that are capable of photosynthesis. The term, therefore, does not include microorganisms, such as bacteria and fungi. The term "plant cell" includes any cell derived from a plant, including undifferentiated tissue, such as callus and plant seeds.

SUMMARY OF THE INVENTION

Accordingly, the object of the present invention is to provide a new tool to accelerate the growth rate of higher plants by transforming cells of higher plants with the TCTP gene. Such transgenic plants exhibit several desirable agronomic phenotypes. Since these transgenic plants have reduced transition time from seedlings to adult plants, they are less exposed to pathogens and environmental stress. This is a critical agronomic trait that significantly improves the productivity of economically important plants. The transgenic plants also have higher commercial value since they can be marketed earlier than the parental plants. While any agronomic plants can be subject to this manipulation to achieve embodiments of this invention, preferred plants could include cabbage, carrot, lettuce, spinach, onion, green onion, cucumber, tomato, potato, radish, tobacco, rice, cauliflower, melon, and watermelon. Woody plants also could be potential targets for this manipulation.

Provided also are transgenic higher plants that are more readily accessible to the *Agrobacterium*-mediated transformation. At least 2 times more calli are induced from the transgenic tobacco plants than from the parental plants under the identical experimental conditions. Furthermore the regeneration rate is much faster. These traits can be exploited in a way that cells of higher plants harboring the TCTP gene can be readily and efficiently transformed with transforming vectors containing other useful genes.

Also, provided includes an uninterrupted gene sequence encoding the ntTCTP protein, a nucleic acid fragment that can be directly ligated into recombinant DNA constructs, and ntTCTP expression vectors which can be used to transform cells of higher plants according to the invention.

This invention can be further utilized to improve the stability of recombinant proteins by fusing the TCTP polypeptide to a protein of interest. Many recombinant proteins, when overexpressed and purified from recombinant expression systems, are unstable and tend to be degraded, a troublesome difficulty frequently encountered with recombinant DNA technology. The recombinant ntTCTP protein expressed in *E. coli* is very stable against heat, salt, and pH and can be readily handled even at room temperature without any serious degradation and aggregation problems.

BRIEF DESCRIPTION OF THE DRAWINGS

FIG. 2 shows a multiple alignment of the deduced amino acid sequences of TCTP homologs from animals, yeast, and plants. The sequences were either extracted from GenBank (G, see below) or assembled from expressed sequence tags (E, see below). Gaps were introduced to maximize sequence homologies. The amino acid sequences were aligned using the PIMA 1.4 program (Baylor College of Medicine, Houston Tex.). The order of sequences in the alignment represents the degree of homology between sequences. TCTP proteins can be classified as three groups based on their relative sequence homologies; plant TCTPs, animal TCTPs, and yeast TCTPs. The basic domain that interacts with tubulins is boxed. The TCTP proteins aligned are; Alfalfa (G, P28014), Arabidopsis (G, AF215897), Chicken (P43347), Fission yeast (Q10344), Human (G, NP 003286), Mouse (G, P14701), Pea (G, P50906), Pharbitis (G, AB007759), Pine (E, AA739699+AA556254), Potato (G, P43349), Rabbit (P43348), Rice (G, P35681), and Yeast (NP 012867).

FIG. 3 shows the specific interaction between the ntTCTP and the Pra3 small GTPase. The wild type (Pra3WT), constitutively active (Pra3QL), and dominant negative (Pra3SA) forms were used as baits in yeast coexpression assays. The Pra3QL and Pra3SA are assumed to bind GTP and GDP in vivo, respectively. Panel A shows the interaction assay in the presence of 20 mM aminotriazole, and Panel B without aminotriazole. 1; Pra3QL and ntTCTP, 2; Pra3SA and ntTCTP, 3; Pra3WT alone, 4; Pra3QL alone, 5; Pra3SA alone.

FIG. 4 shows the physical maps of the pBI-TCTP expression constructs. The expression vector constructs were generated by incorporating the full-size ntTCTP gene into the 35S-based vector (Clonetech, Palo Alto, Calif.). The ntTCTP gene was inserted in both orientations (referred to as S (sense) and AS (anti-sense)). For Pra3 expression, the pea pra3 ORF was incorporated into the vector in the same way as with the ntTCTP gene to generate the pBI-Pra3. BamHI and SacI restriction sites were used for cloning of both ntTCTP and pra3 genes into the vectors.

FIG. 5 shows the transgenic tobacco plants overexpressing the ntTCTP genes. Plants were grown for 2 weeks in the light after germination. S; Sense orientation, AS; anti-sense orientation, C; control plant transformed with the original vector alone. Note that the leaves of transgenic plants have dark green color.

FIG. 8 is a Northern blot analysis showing the effects of exogenously applied plant growth hormones on the ntTCTP mRNA accumulation. Plants were first grown for 10 days on the MS agar plates, then transferred into MS agar bottles, and grown for additional 18 days. The plants were then soaked in a liquid medium containing an appropriate hormone and gently shaked for 24 hours before harvesting plant materials. C; untreated, G; GA3, P; PEG, I; IAA, K; kinetin, A; ABA. Fifteen percent of PEG and 2 μM of each hormone were used. The bottom panel shows the ethidium bromide-stained rRNA bands as used in FIG. 7.

DETAILED DESCRIPTION OF THE INVENTION

The present invention provides methods of up- or down-regulating the intracellular TCTP levels in plant species of interest by introducing the nucleic acid fragment containing an uninterrupted coding sequence for the TCTP protein. The nucleic acid fragment is first manipulated operationally functional in a desired plant species by its fusion to a genetic sequence capable of promoting the expression of the TCTP coding sequence and to a polynucleotide sequence capable of regulating polyadenylation signals for proper RNA processing. When such a combined nucleic acid fragment is introduced into a plant of interest, the expression of the TCTP is up- or down-regulated. This results in modifications of plant growth and developmental characteristics, such as accelerated growth rate in earlier growth stage, dark green leaf, and robust stems. These agronomic traits are of great values in agriculture since plants in the transition stage from seedling to young plant are very vulnerable to environmental stress and pathogenic attacks. The TCTP can be employed to engineer various agronomic plants so that the transgenic plants grow faster and healthier in earlier growth stage. In addition, the transgenic plants can be marketed earlier than the parental plants, an efficient way to save labor and time required for plant agriculture.

This invention also provides a method of improving the transformation efficiency and regeneration rate of desired plants of scientific importance by introducing the TCTP coding sequence into these plants. This trait could be critical especially when plants that are reluctant to genetic engineering are to be transformed. The higher plants transformed with the TCTP gene is more efficiently transformed than the parental plant in the second round transformation. In addition, more calli are induced and the calli grow much faster. This characteristic is very useful when a large number of transgenic plants should be regenerated from a single transformation, especially when a mutant seed pool is to be collected by the T-DNA insertion method (Hayashi et al. 1992) or by the activation tagging method (Walden et al. 1994). It is envisioned that the introduction of the TCTP gene into other useful plants will make them more accessible to genetic engineering.

The present invention provides methods of identifying a nucleic acid fragment encoding the TCTP protein from Nicotiana tabacum, and of introducing it into genetically engineered plants to modify growth and developmental characteristics for the improvement of agronomic and commercial value. We originally identified the pea TCTP protein (referred to as psTCTP in this work) by yeast two-hybrid screens as a Pra3 small GTPase interacting protein. To more systemically investigate the TCTP-Pra3 interaction in tobacco plants, a full-size ntTCTP cDNA coding sequence is isolated by the reverse transcriptase-polymerase chain reaction (RT-PCR) using tobacco mRNA and 5′- and 3′-specific primer pair. The PCR primers are designed by aligning all known plant TCTP gene sequences. The ntTCTP gene consists of 504 bp and encodes a polypeptide of 168 amino acids with a predicted molecular mass of 18.7 kDa. The ntTCTP protein is expressed as a GST fusion in E. coli cells. The ntTCTP physically interacts with the Pra3 small GTPase in a GTP-dependent manner. The predicted ntTCTP polypeptide is a highly acidic protein with a calculated isoelectrical point (pI) of 4.36, like other TCTP proteins from animals and plants.

A nucleic acid fragment encoding the TCTP polypeptide can be isolated as a full-size cDNA clone either by the conventional RT-PCR method using mRNA as template or by the screening of a cDNA library using a partial-size cDNA fragment, if available, as probe. The RT-PCR method can be applied for the isolation of the ntTCTP gene since plant TCTP genes are highly conserved (70–75% homology among plant TCTP genes). For the RT-PCR method, the poly(A)+ mRNA is first converted into a primary cDNA using reverse transcriptase and oligo(dT)$_{16-18}$ as primer, and an uninterrupted double stranded cDNA is subsequently synthesized by PCR using a pair of specific primers, a molecular biological technique well-known to the art.

The expression pattern of the TCTP gene is examined by hybridization with the radiolabeled TCTP polynucleotide molecule which is either RNA or DNA molecule. The RNA probe is synthesized from a DNA template by in vitro transcription using SP6 or T7 RNA polymerase, a well-known technical procedure in the art. The DNA probe is synthesized in several different ways, such as end-labeling, nick translation, and random prime labeling systems, depending on the amount of substrate available, the size of substrate, and the desired specificity of the probe, etc. The probe used in this work is a random prime labeled probe synthesized from the full-size TCTP cDNA molecule. In Northern hybridization, total RNA is isolated from different plant tissues by any of a number of standard procedures and subject to a denaturing agarose gel electrophoresis. The RNA in the gel is transferred to nylon or nitrocellulose membranes and detected with an appropriate radiolabeled probe Northern hybridization is also employed to investigate the effects of growth hormones and light on the TCTP gene expression. To do this, plants are grown on MS media containing different plant growth hormones at physiological concentrations, and total RNA is isolated from plant tissues and processed as described above. The ntTCTP gene expression is not affected by exogenously applied plant growth hormones but is remarkably induced (7–8 fold increase) by a 15% PEG treatment which mimics the drought stress condition. However its expression is not significantly affected by light.

According to the present invention, the ntTCTP polypeptide is produced by recombinant DNA technologies, such as those generally described in MOLECULAR CLONING—A LABORATORY MANUAL (Maniatis et al., Cold Spring Harbor Laboratory, 1989). Selected methods suitable for DNA manipulation and expression of the TCTP are described in detail in the Materials and Methods. The ntTCTP polynucleotide molecule shown in FIG. 1 can be cloned into an appropriate expression vector and expressed in recombinant expression systems, such as prokaryotes, yeast, or insect cells. Gene fusion strategies also can be used to achieve improved proteolytic stability, solubility, and efficient recovery of the recombinant proteins. The recovery of the fusion protein can be simplified if the fusion tag has an affinity for a specific ligand. For example, HIS tag/$Ni^{2+}$, Strep tag/streptavidin, MBP/amylose, GST/glutathione, and CBP/chitin are frequently used fusion partner/ligand pairs in the recombinant DNA technologies (Nygren et al. 1994). In this work the glutathione S-transferase (GST) polypeptide is fused to the N-terminus of the ntTCTP polypeptide. The recombinant GST-ntTCTP fusion protein is expressed in *E. coli* strain BL21 and purified using Glutathione Sepharose 4B. One of the suitable expression vector systems in *E. coli* in this context is the pGEX-4T-2 (Amersham Pharmacia) into which the ntTCTP gene is ligated, and the expression vector construct is introduced into *E. coli* strain BL21.

The ntTCTP polypeptide is efficiently expressed to a high level (25–30 mg per liter culture) in *E. coli*, and more than 90% of the expressed protein is recovered in a soluble form. The recombinant ntTCTP polypeptide is stable throughout the purification steps and resistant to proteolytic degradation. This characteristic can be utilized to stabilize recombinant proteins expressed in recombinant expression systems. For this purpose, the DNA molecule encoding the ntTCTP polypeptide, as a full-size or a partial-size sequence, is in frame fused to a gene sequence of interest. When expressed in *E. coli*, this gene fusion may result in a fusion protein whose expression level, solubility, and stability are markedly improved.

Most of the recombinant DNA technologies used in this invention are known to those skilled in the art. The present invention is further described with references to the following detailed examples. These examples are provided here only for illustration purposes and not intended to be limiting unless otherwise specified.

Materials and Methods
Plants Materials

Seeds of *Nicotiana tabacum* (Petit Havana SR1) were surface-sterilized in 70% ethanol for 15 seconds and subsequently soaked in 20% clorox solution for 10 min. The seeds were then thoroughly rinsed with sterile distilled water at least ten times. The sterile seeds were plated on 0.8% Phytoagar (Duchefa, Haarlem, The Netherlands) plates containing 0.5× Murashige and Skoog (MS) salt supplemented with 1.5% sucrose and grown in a culture room at 25° C. with a 16-hour photoperiod. For hormone treatments, plants were first grown for 10 days on MS agar plates in the light, transferred to agar bottles, and further grown for additional 18 days. The young plants were then soaked in liquid media containing different hormones at appropriate concentrations for 24 hours before harvesting plant tissues. Each hormone was used at a final concentration of 2 $\mu$M, and PEG was used at 15% (w/v). Hormones tested in this work include giberellic acid (GA3), indole-3-acetic acid (IAA), kinetin, and abscisic acid (ABA). For light treatments, plants were grown for 3 weeks under the normal light condition and divided into two groups and further grown for 7 days either in the light or in the dark.

Enzymatic Treatments of DNA

Routine DNA manipulations were performed according to Maniatis et al (1994) with some modifications whenever necessary. Restriction digestions were usually done in 20 $\mu$l reaction volumes with enzyme of 1–5 units per microgram of DNA, and the mixtures were incubated at an appropriate temperature for 1–2 hours. Each restriction digestion usually contained 1–3 $\mu$g plasmid DNA. Enzyme digestion buffers used were those supplied by the manufacturer for each particular enzyme unless specified. For ligation reactions, DNA fragments, either a digestion mixture or a PCR product, were first separated on 0.8–1.5% agarose gels, depending on the sizes of the DNA fragments of interest. The desired DNA fragment was purified from the gel piece using either the GENECLEAN II Kit (BIO 101, Vista, USA) or the Gel Extraction Kit (Omega Biotek, Doraville, USA). The vector and insert fragments were mixed at the molar ratio of 1:1 to 1:3 in a 10 $\mu$l volume using the buffer supplied by the manufacturer, and the mixture was incubated at 13–16° C. for 5 hours (for sticky-end ligations) or 12 hours (for blunt-end ligations). T4 DNA ligase and its corresponding ligase buffer (NEB, Beverly, USA) were routinely used with 5–10 units of ligase per 10 $\mu$l volume reaction. To render the ends of DNA fragments blunt prior to ligation, T4 DNA polymerase and its corresponding buffer (NEB) were used. The mixture was incubated at 25° C. for 15 min and heated at 65° C. for 10 min to inactivate the enzyme, and the DNA fragment was gel-purified as describe above.

*E. coli* Transformation

*E. coli* strain XL1-blue was routinely used as host cells for the transformation with plasmid DNAs. The competent cells were prepared in the laboratory as described (Hanahan 1985). One to five microliter of the ligation mixture was used to transform 100–200 $\mu$l of competent cells. After incubation of the mixture on ice for 20 minutes, it was heat-shocked at 42° C. for 2 minutes, and 1 ml of SOC medium was added. The mixture was then gently shaked at 37° C. for 1 hour to render the cells recovered from damage, and 100–200 $\mu$l was spread on LB plates containing an appropriate antibiotic. The plates were incubated at 37° C. overnight or until positive colonies were visible.

Plasmid Isolation and Purification

The alkaline-SDS method was used to isolate plasmid DNA from *E. coli* culture as described (Kraft et al. 1988). A 3 ml (for high copy number plasmid) or a 20 ml LB culture (for low copy number plasmid) was routinely prepared for the small scale purification of plasmid DNA. A single colony was inoculated into LB liquid medium containing an appropriate antibiotic and incubated at 37° C. with vigorous shaking overnight. When a large amount of plasmid DNA is required, TB medium (Terrific broth, 47.6 grams of TB mix per liter, Difco, Detroit, USA) was used instead of LB medium. The cells were harvested by centrifugation for 10 seconds in an Eppendorf centrifuge, and the cell pellet was rinsed with distilled water before cell lysis. To prepare plasmid DNA for DNA sequencing and *Agrobacterium* transformation, it was purified using the Plasmid Miniprep Kit II (Omega Biotek). For large scale purifications, up to 500 ml of *E. coli* culture was prepared.

Yeast Two-Hybrid Screening

Yeast two-hybrid screening was carried out using the MATCHMAKER Two-Hybrid System (Clonetech). The pea pra3 gene was cloned into the bait plasmid pGBT9, resulting in the pGB-pra3. In this vector construct the pra3 gene is in frame fused to the DNA sequence encoding the GAL4 DNA binding domain, and the fusion protein is expressed under the control of the alcohol dehydrogenase gene (ADH1) promoter. A pea cDNA library was constructed from 5 day-old dark-grown plants. About 10 grams of plant material was first homogenized in 20 ml of GTC buffer (4M GTC, 50 mM Tris.Cl, pH7.5, 10 mM EDTA; 5 mM Sodium acetate, 0.1 M 2-mercaptoethanol) supplemented with 1 ml PVP and 1 ml of 10% Sarcosyl. The homogenate was divided into two Falcon tubes and 0.1 volume of 2M sodium acetate (pH 4.0) was added to each tube. After vigorous shaking with 1 volume of the phenol:chloroform:isoamyl alcohol (25:24:1), it was centrifuged at 10,000×g for 15 minutes at 20° C. The supernatant was mixed with NaCl at a final concentration of 2M and incubated at room temperature for 30 minutes, and RNA was precipitated with 0.8 volume of ice-cold isopropanol at −20° C. overnight. RNA was recovered by centrifugation and reprecipitated three times with 4M LiCl. The total RNA pellet was rinsed with 70% ethanol two times and desiccated. The poly(A)+ mRNA was isolated from total RNA using the Oligotex mRNA Spin Column (Qiagen) as described by the manufacturer. The cDNA was synthesized using the cDNA Synthesis Kit (Stratagene, La Jolla, USA) and cloned into the pAD-GAL4-2.1 phagemid vector using the HybriZAP-2.1 Two-Hybrid Predigested Vector/ Gigapack Cloning Kit (Stratagene, La Jolla, Calif.). The average size of the cDNA inserts was about 1.5 kbp, and the primary library size was $1.25 \times 10^6$ pfu. The pGB-pra3 bait plasmid was first transformed into yeast strain HF7c by the LiAc method, and the selected transformant was subsequently transformed with the cDNA library plasmids. The final transformants were selected on SD plates lacking leucine/tryptophane/histidine in the presence of 20 mM aminotriazole to eliminate false positives. Plasmids were isolated from the positive clones and electroporated into $E.$ $coli$ strain HB101 to amplify the plasmid DNA.

Isolation of the Full-size TCTP cDNAs from Pea and Tobacco Plants

A cDNA fragment encoding the C-terminal region of the pea TCTP (pcTCTP) protein was first identified through a yeast two-hybrid screen. The cDNA fragment was then used as probe to isolate the full-size cDNA clone by screening a pea cDNA library synthesized from dark-grown pea seedlings. A tobacco TCTP homolog gene was also isolated by the RT-PCR method. A tobacco TCTP cDNA sequence (GenBank accession no. AB001558) was first identified from the database of the expressed sequence tags (EST), which contained the 5' sequence region of the tobacco TCTP gene, including the authentic start codon. Based on the nucleotide sequence, the 5' primer was designed as 5'-CGC GGA TCC ATG TTG GTT TAT CAG GAT C-3' (SEQ ID NO:3) and had a BamHI restriction site (bold). An oligo $(dT)_{18}$ was first used as primer for the reverse transcription of the tobacco poly(A)+ mRNA. The primary cDNA was then used for PCR amplification using the 5' and oligo(dT)$_{18}$ primer pair and PfuTurbo polymerase that has a proofreading activity (Stratagene). The PCR profiles were 25 cycles each at 94° C. for 1 minute, at 60° C. for 1 minute, and at 72° C. for 2 minutes, and one cycle at 72° C. for 10 minutes. The PCR product was cloned into the SmaI-digested pGEM-3Z(+) vector (Promega, Madison, USA) for DNA sequencing and further manipulation.

DNA Sequencing and Sequence Analysis

All full-size and partial-size cDNA fragments and the junctions of the expression vector constructs were confirmed by DNA sequencing on both strands. DNA sequencing was carried out using the ABI PRISM 310 Genetic Analyzer (Perkin Elmer, Foster City, USA) as described in the manufacturer's manual. For each sequencing run, about 500 ng of plasmid DNA and 2–4 picomoles of 15–17 mer sequencing primer were used. Computer-assisted sequence analysis was performed using the BLAST program (NCBI, USA).

In Vitro Mutagenesis

The QuickChange™ kit (Stratagene) was used for in vitro mutagenesis of the pea pra3 gene as described by the manufacturer. A pair of pra3-specific complementary mutagenic primers was used for each substitution. The two complementary primers used for the S31A substitution (a dominant negative form) were 5'-CCG CCG TGG GGA AAG CAC AGA TAC TAG CTA-3' (SEQ ID NO:5) (+ strand) and 5'-CTA GCT AGT ATC TGT GCT TTC CCC ACG GCG G-3' (SEQ ID NO:6) (− strand). The two mutagenic primers are complementary to each other, including the substituted bases. The original TCA codon (Ser) was mutated to the GCA codon (Ala) (bold). The mutagenic primers for the Q76L substitution (a constitutively active form) were 5'-CTG GGA TAC CGC TGG TCT AGA ACG ATA TAG AGG AG-3' (SEQ ID NO:7) (+ strand) and 5'-CTG CTC TAT ATC GTT CTA GAC CAG CGG TAT CCC AG-3' (SEQ ID NO:8) (− strand). The original GAA codon (Gln) was mutated to the CTA (Leu). Mutated sequences were verified by DNA sequencing on both strands.

RNA Isolation and Northern Blot Analysis

Total RNA samples were isolated from appropriate plant tissues using the Rneasy Plant Total RNA Isolation Kit (Qiagen) according to the procedure supplied by the manufacturer. In most Northern gels, 10–20 µg of the total RNA was loaded onto each lane. RNA samples were first denatured in MOPS buffer(20 mM MOPS, 8 mM sodium acetate, 1 mM EDTA) supplemented with 50% (v/v) formamide and 2.2 M formaldehyde at 65° C. for 10 min and fractionated on a 1% agarose gel prepared in the same buffer used for sample denaturation. The gel was then transferred onto a Hybond-N nylon membrane (Amersham) in 20×SSC buffer overnight. The membrane was prehybridized in the Quick-Hyb solution (Stratagene) containing 200 µg/ml of denatured, sheared calf thymus DNA at 65° C. for 1.5 hours. The probes were $P^{32}$-labeled gene fragments generated by random priming in the presence of isotope. The radio labeled probe was added, and the membrane in the solution was further incubated at 65° C. for 18 hours. The membrane was then washed in 2×SSC/0.1% SDS two times at room temperature, in 1×SSC/0.5% SDS at 65° C. for 15 minutes, and subsequently in 0.5×SSC/0.1% SDS at 65° C. for 15 minutes or until the background activity is undetectable. The membrane was exposed to X-ray films for 2 to 16 hours, depending on the radioactive counting of the filter.

Expression and Purification of the Recombinant ntTCTP in $E.$ $coli$

The TCTP proteins were expressed using the GST Gene Fusion System (Amersham-Pharmacia). The full-size pcTCTP and ntTCTP gene sequences were reamplified from the pGEM-T easy vector constructs by PCR. The 5' PCR primer was 5'-CGC GGA TCC ATG TTG GTT TAT CAG GAT C-3' (SEQ ID NO:3) for both genes and had a BamHI site (bold). The 3' PCR primers were 5'-CTC GTC GAC GCA CTT GAT CTC CTT GAA AG-3' (SEQ ID NO:9) for psTCTP and 5'-CTC GTC GAC ACA CTT GAC CTC CTT GAG-3' (SEQ ID NO:4) for ntTCTP and had SalI sites (bold). The PCR products were double-digested with BamHI and SalI and incorporated into the pGEX-4T-2 $E.$ $coli$ expression vector, resulting in pG-pcTGTP and pG-ntTCTP. In these expression constructs, the TCTP gene sequences are fused in frame to the glutathione S-transferase (GST) sequence at the N-terminus. The vector constructs were transformed into $E.$ $coli$ strain BL21, and the transformants were selected with 100 µg/ml ampicillin. RB medium, rather than LB, was used for induction (Lamparter et al. 1997). Two hundred fifty ml of RB (0.5% yeast extract, 1% tryptone, 0.5% NaCl, 0.2% glucose, pH 7.5 with NaOH) supplemented with ampicillin (100 µg/ml) was inoculated with 3 ml of freshly grown cell culture and incubated at 30°

C. with shaking at 250 rpm to an $OD_{600}$ of 0.6. Expression was induced by adding IPTG (1 μM) and by further shaking at 30° C. for 3 hours. After centrifugation at 5000×g for 5 minutes, the cell pellet was washed in ice-cold 1×Phosphate-Buffered Saline (PBS, 140 mM NaCl, 2.7 mM KCl, 10 mM $Na_2HPO_4$, 1.8 mM $KH_2PO4$, pH7.3). The cells were then resuspended in 5 ml of 1×PBS and lysed by repeated sonications on ice (with output of 4–5, 30 seconds×4 times). The homogenate was clarified by ultracentrifugation at 100,000×g for 30 minutes. The crude extract was concentrated 5 times using Amicon microfilter (Centriprep YM 30, Milipore) by centrifugation at 3000×g for 2–4 hours. The GST-TCTP fusion proteins were purified using a Glutathione Sepharose 4B affinity column as described by the manufacturer (Promega). The purified fusion proteins were then subject to thrombin digestion to remove the GST tag. Ten μl of thrombin solution (1 cleavage unit/μl) per mg fusion protein was added, and the mixture was incubated at 0–37° C. for 15 hours either in the presence or absence of 10 μM $Ca^{2+}$. The TCTP protein was finally separated from the GST tag by a second run of the Glutathione Sepharose 4B affinity column.

Gel Electrophoresis of DNA and Protein

Agarose gel electrophoresis of DNA was usually performed using gels with a concentration range of 0.8–1.5%, depending on the size of the DNA fragments being analyzed, using the TAE buffer (40 mM Tris-acetate, 1 mM EDTA, pH8.0). Electrophoresis was performed at a voltage rage of 50–200, depending on the amount of DNA loaded onto wells, for a desired time or until DNA fragments were well separated. The gel was stained with 0.5 μg/ml ethidium bromide solution, visualized on an UV transilluminator, and photographed if required.

All protein preparations and purification steps were monitored by 12–15% SDS-PAGE gels using the Hoefer Mighty Small II system (Amersham Pharmacia). Electrophoresis was performed at a constant voltage set with a range of 80–120 volts for a desired time. The gel was stained with 0.25% Coomassie Brilliant Blue R250 for visualization.

Construction of Plant Expression Vectors

The TCTP sequences in the pG-pcTCTP and pG-ntTCTP were double-digested with BamHI and SalI. The pBI121 (Clonetech, Palo Alto, USA) was also double-digested in an identical way. The DNA fragments were then blunt-ended with T4 DNA polymerase (NEB) and ligated using T4 DNA ligase (NEB), resulting in the pBI-ntTCTP-S (sense orientation) and pBI-ntTCTP-AS (anti-sense orientation). The vector fragment was dephosphorylated using alkaline phosphatase (NEB) before ligation. The pra3 gene was also cloned into the pBI121 vector in a similar way.

Plant Transformation

The plant expression constructs were transformed into tobacco plants via the *Agrobacterium tumefaciens* infection of leaf disks essentially as described (Horsch et al. 1985). Briefly, leaf disks, 7 mm in diameter, were cut out from young plants grown in a sterile condition using a sterile paper punch. They were put on MS agar plates (0.8% agar, pH5.8) supplemented with 1.5% sucrose, 0.1 ml of 1 mg/ml NAA, and 1 ml of 1 mg/ml BAP per liter, inoculated with the *Agrobacterial* cells carrying the plasmid of interest, and incubated for 3 days under mixed fluorescent and white lights in a growth chamber set at 25° C. Leaf disks were then transferred onto fresh MS agar plates with the same composition as those used for *Agrobacterium* infection but further supplemented with 200 mg/ml kanamycin and 500 mg/ml cefotaxime and incubated for 3–4 weeks until small shoots develop. The small shoots were excised with a sterile scalpel and planted in hormone-free MS agar bottles supplemented with 1.5% sucrose and 200 mg/ml kanamycin. Shoots that can root into this medium in 2–3 weeks were selected and grown in soil. Homozygotic lines were isolated from each transgenic plant by repeated kanamycin selections.

Results

Plant TCTP: a Small GTPase Interacting Protein

Small molecular weight GTPases (small GTPases) are members of the diverse Ras superfamily GTP binding proteins. They function as on/off molecular switches (Ma 1994) in various cellular signal transduction (Marshall 1993; Hall 1990), cytoskeletal organization (Hall 1990), and vesicular transport (Lazar 1997), although their molecular mechanisms have not been fully clarified yet in most cases. As an effort to further understand the molecular mechanism for the functions of small GTPases in plants, we carried out yeast two-hybrid screens using the Pra3 small GTPase as bait and a pea cDNA library constructed from dark-grown seedlings.

Among the 26 positive colonies, 7 colonies contained the pea TCTP gene sequence. The determined nucleotide sequence of the pea TCTP coding region (referred to as pcTCTP) is completely identical to that registered in the GenBank database (accession no. L47968). The amino acid sequence of the pcTCTP is shown in FIG. 2 in an alignment with other TCTP proteins. Together with the involvement of the Pra3 in the phytochrome-mediated light signal transduction and the suggested role of the TCTP in cell proliferation (Gachet et al. 1999), it was implicated that at least some of the phytochrome-mediated light signals are transmitted to the TCTP protein via the Pra3 and regulate plant growth and development.

Isolation of Tobacco TCTP cDNA

Figure 1:
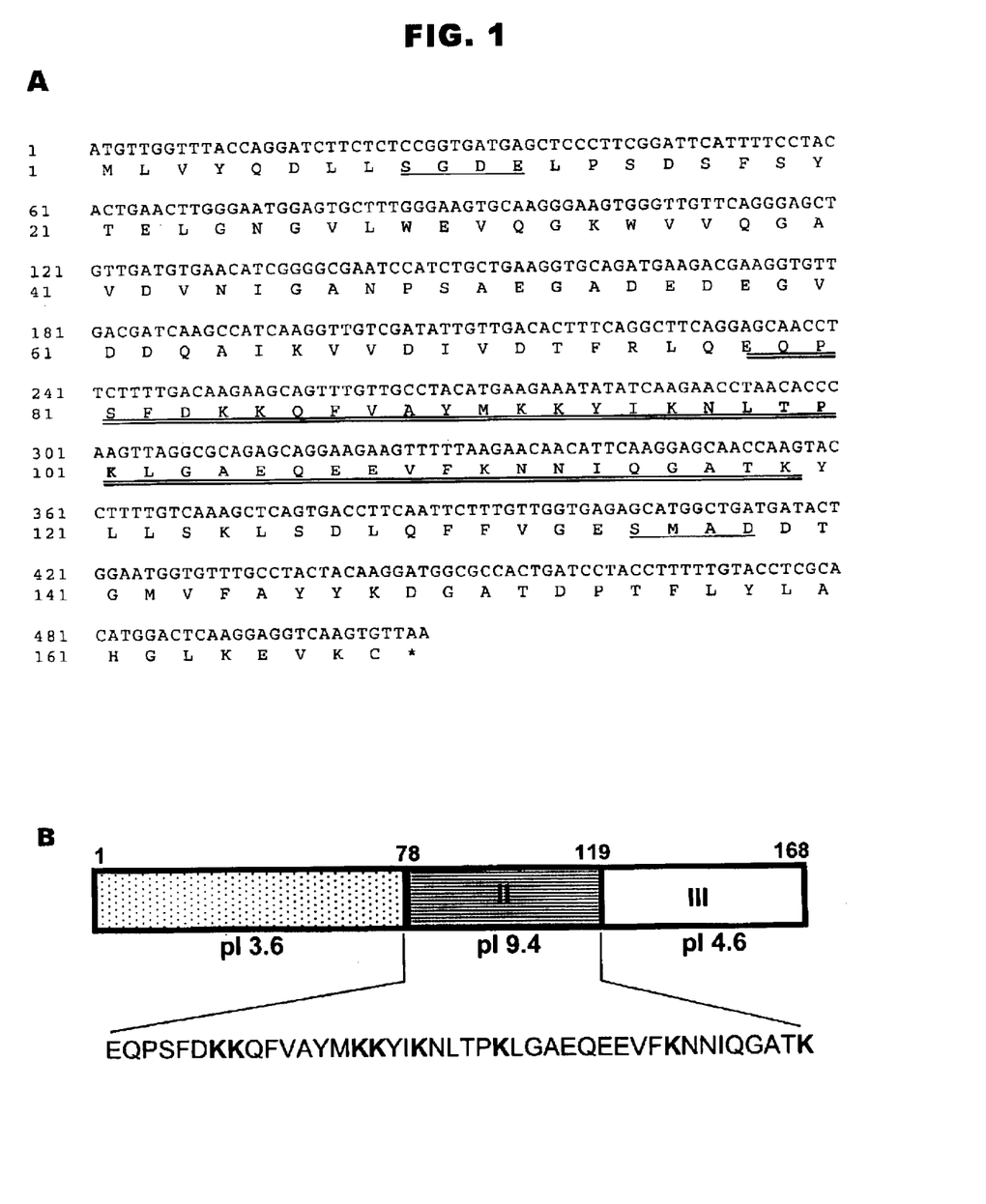
FIG. 1 shows the nucleotide sequence of a tobacco cDNA clone (GenBank accession no. AF107842) encoding the ntTCTP protein (A) and its domain structure (B). (A) The putative CKII-dependent (single underlined) and PKC-dependent (bold face) phosphorylation sequences are indicated. The basic domain, which is involved in the interaction with tubulins, is double underlined. The asterisk represents the termination codon. (B) Three domains in the ntTCTP protein are indicated as I, II, and III with predicted pI values, respectively. The amino acid sequence of the basic domain II is given with lysine residues in bold face.

Plant TCTP proteins seem to be encoded by a single-copy gene in most plants (Woo et al. 1997). Sequence analysis of the plant TCTP genes and gene fragments found in the GenBank database also support this notion. All TCTP polynucleotide sequences deposited in the database from a single plant species are identical. We therefore decided to identify the TCTP gene homolog from tobacco plant with which transformation and tissue culture systems are well established. Search for tobacco TCTP gene sequence in the databases identified an expressed sequence fragment (AB001558) that encoded the N-terminal region of the putative tobacco TCTP, including the start codon. We designed the 5' PCR primer from the sequence information, and RT-PCR was carried out using the 5' and oligo(dT)$^{18}$ primer pair and total RNA isolated from dark-grown tobacco plant to isolate the full-size tobacco TCTP cDNA clone. The RT-PCR run amplified a single dominant band of 703 bp, including the 3' nontranslating sequence. The determined nucleotide and the predicted amino acid sequences are shown in FIG. 1A and deposited in the GenBank database (accession no. AF107842). Computer-assisted sequence analysis confirmed that it encodes the bona fide tobacco TCTP. Southern blot analysis showed that the tobacco genome contains a single-copy TCTP gene (data not shown). We also obtained the same Southern blot result from the pea plant. A single band was detected in Southern blot analysis using the genomic DNA preparations digested with restriction enzymes whose recognition sequences were not present in the pea TCTP gene. These observations are also consistent with the previous result with the Japanese morning glory plant (Woo et al. 1997) and further support that most plants, if not all, have a single-copy TCTP gene.

Domain Structure of the ntTCTP Protein

The tobacco TCTP coding sequence (referred to as ntTCTP gene) consists of 507 bp, including the stop codon, and encodes a polypeptide of 168 amino acids with a calculated molecular mass of 18.7 kDa (FIG. 1A). The ntTCTP has about 50–70% protein sequence identity to other TCTP proteins from animals, yeast, and plants and contains all the highly conserved TCTP-specific structural motifs. The ntTCTP has the highest amino acid sequence homology to those from rice and Japanese morning glory (FIG. 2). One structural characteristic of the ntTCTP is its three-domain organization based on the calculated isoelectrical point (pI) of each domain, as shown in FIG. 1B. Domains I and III are highly acidic with pI values of 3.6 and 4.6, respectively. On the contrary, domain II is highly basic with a pI value of 9.4. A basic domain of the mouse TCTP corresponding to the domain II of the ntTCTP has been shown to bind to tubulins (Gachet et al. 1999). The TCTP proteins are highly conserved among different organisms and do not show any detectable similarity to other known proteins or conserved motifs. It is noticeable that the TCTP proteins can be classified as three groups, one group from plants, the second from animals and the third from yeast. In each group the protein sequence homology increases up to higher than 80%. Each group has unique domains that are highly conserved within the group but somewhat diverse from those of other groups, such as those of amino acid regions 35–45, 77–90, and 104–135. It is of particular interest that the three TCTP subgroups are most diverse in the domain II that also includes the amino acid regions 77–90 and 104–135. Although the TCTP proteins are suggested to have a common role in different organisms, this structural characteristic suggests that the domain II may be involved in the determination of phylum-specificity. All together, these observations suggest that TCTP proteins have evolved from a common ancestor and may have identical or similar physiological function(s) in different organisms.

Interaction Between ntTCTP and Pra3 Small GTPase

Figure 3:
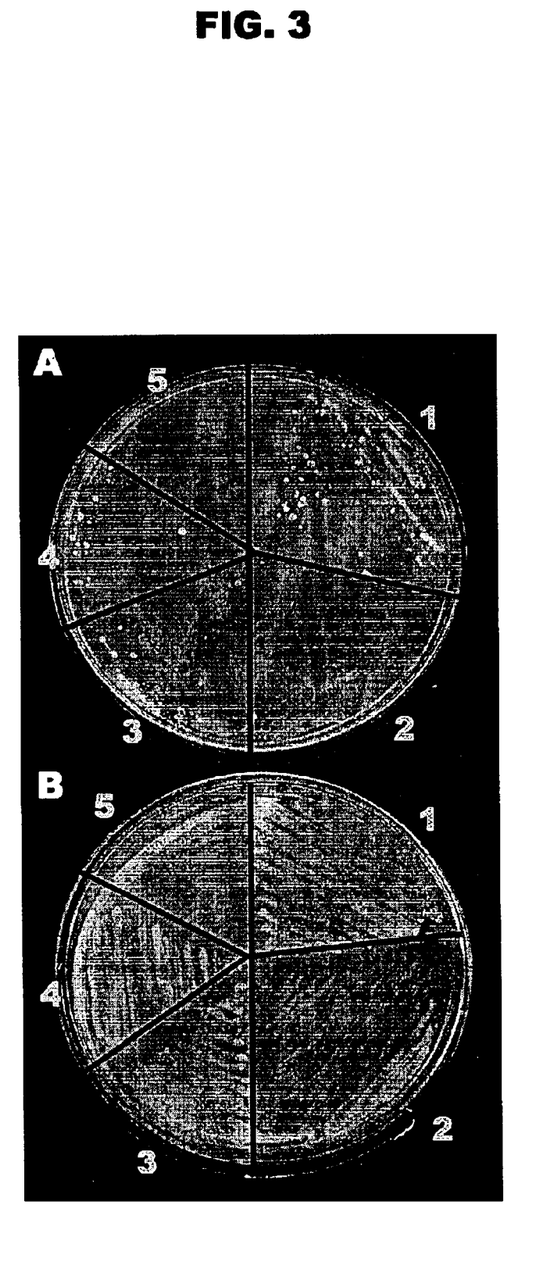

The psTCTP was first identified as a Pra3 interacting protein through yeast two-hybrid screens. To examine if the ntTCTP also interacts with the Pra3, two mutant forms of the Pra3 were generated and the ntTCTP-Pra3 interactions were examined by yeast coexpression analysis. The Ser-31 of the Pra3 was substituted with Ala to generate a dominant negative Pra3 (GDP-bound form). The Gln-76 was substituted with Leu to generate a constitutively active Pra3 (GTP-bound form). The ntTCTP gene was fused to the GAL4 DNA-binding domain in the pGBT9 vector, and the pra3 genes were fused to the GAL4 activation domain in the pGAD424 vector. The vector pair were then cotransformed into the yeast strain HF7c. To minimize any self-activation, 20 mM 3-amino-,2,4-triazole was included in SD media. One such result is shown in FIG. 3.

The ntTCTP interacted more strongly with the constitutively active Pra3 (Pra3-Q76L) than with the dominant negative form (Pra3-S31A). An identical interaction pattern was observed between the psTCTP and Pra3 proteins in similar analyses, suggesting that the TCTP-Pra3 interaction is not unique to the pea plant but probably functional in all plant systems.

Transgenic Plants Overexpressiong ntTCTP gene

Figure 4:
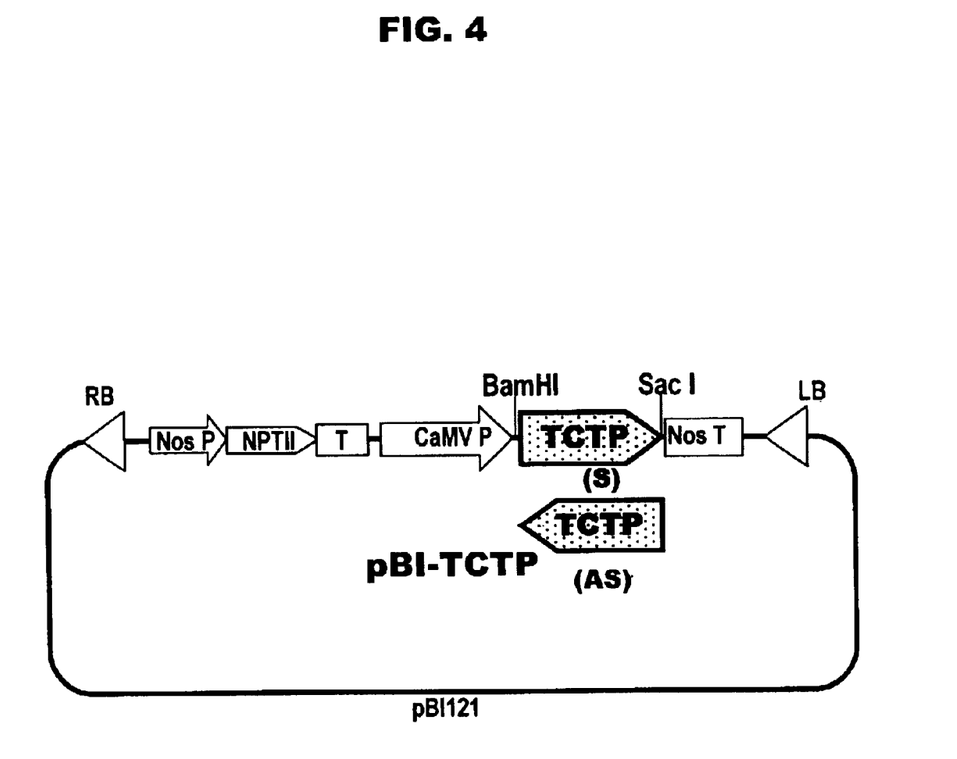

To investigate the physiological role(s) of the plant TCTP, the ntTCTP gene was incorporated into the pBI-based plant expression vector in both orientations (FIG. 4), and the operationally functional constructs were introduced into tobacco plants. Homozygotic transgenic lines were isolated by repeated kanamycin selections. As a control, the vector without insert was also included.

Figure 5:
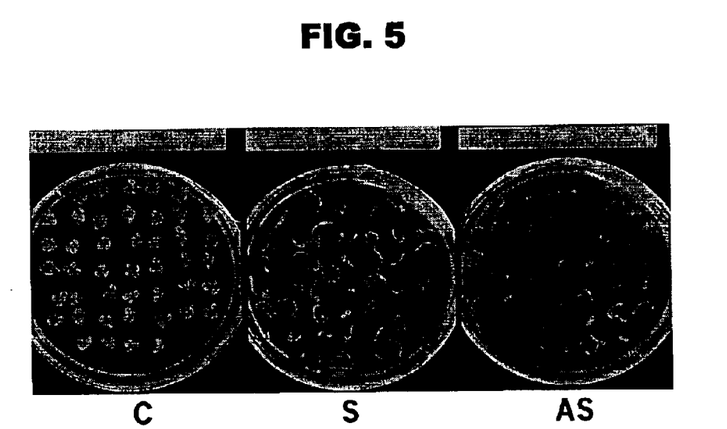

The adult transgenic plants were indistinguishable from the parental plants in terms of plant height, size and shape. They did not show any phenotypic changes. However, more close examination of the transgenic plants through growth stages revealed that the transgenic plants have significantly different growth kinetics. They grew about 30% faster than the parental plants in earlier growth stage from seedlings to young plants (FIG. 5). These indicate that it takes a shorter transition time for the transgenic plants to reach the adult stage than the parental plants. In addition, leaves had dark green color, and stems were thicker than that of the parental plants. These traits are critical agronomic factors since seedlings or young plants are very vulnerable to environmental changes and pathogen attacks, resulting in a great loss of yield. Both sense and anti-sense transgenic plants showed similar phenotypes. Northern blot analysis showed that the transcriptional level of the transgene in the sense transgenic plants was extremely low, most probably due to a cosuppression in the sense transgenic plants (data not shown). These results suggest that the ntTCTP negatively regulate cell proliferation. This is completely contradictory to the suggested role of the TCTP protein in cell proliferation in animals (see below).

We also observed an interesting phenomenon when tobacco leaf disks were infected with Agrobacterial cells containing the ntTCTP gene. More calli were induced when infected with Agrobacterial cells containing the ntTCTP gene than with Agrobacterial cells containing other genes. In addition, the calli grew much faster. To confirm this observation, parental and transgenic plants were subject to callus induction under the identical conditions. Three repeated experiments confirmed that at least 2–3 times more calli were induced from transgenic plants with the ntTCTP gene at an accelerated growth rate. This characteristic can be an important advantage when a large number of transgenic plants or seed pools are required. For example, it is envisioned that any plants harboring the ntTCTP gene could be more readily infected with Agrobacterial cells containing other useful genes.

Figure 6:
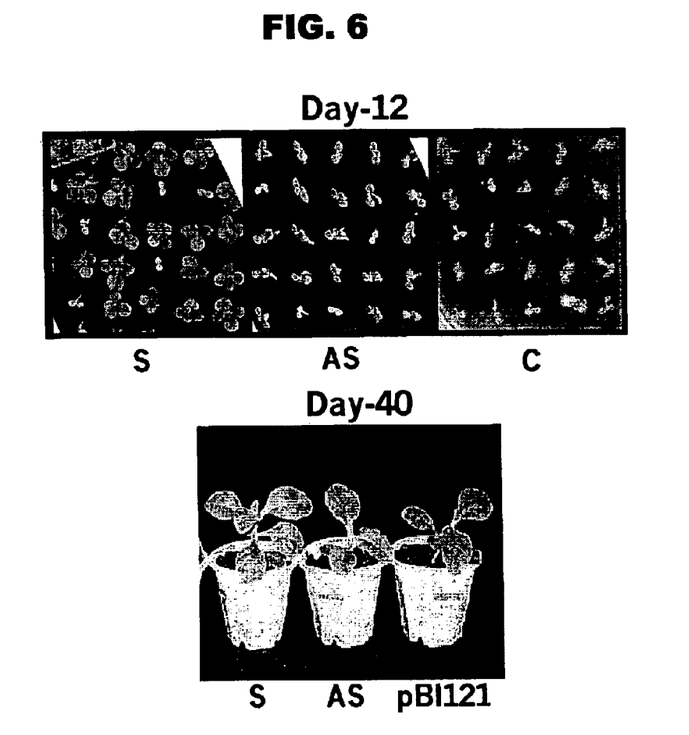
FIG. 6 shows the transgenic tobacco plants overexpressing the pea pra3 gene. Plants were grown for 12 days (upper panel) or for 40 days in the light after germination. S; sense orientation, AS; anti-sense orientation, C; control plant as used in FIG. 5.

The ntTCTP interacts specifically with the constitutively active form of the Pra3, implying that transgenic plants with the pra3 gene would show similar phenotypic alterations. FIG. 6 shows transgenic tobacco plants overexpressing the pra3 gene. The sense transgenic plants grew faster than the parental plant at a similar growth rate and kinetics to those of the ntTCTP transgenic plants. This observation strongly supports that the interaction between the TCTP and Pra3 is involved in the growth regulation in earlier growth stages of plants. The anti-sense transgenic plants did not show such a phenotypic change his may be related to the intrinsic expression pattern of the pra3 gene. The Pra3 is highly expressed in the dark, but the expression level is drastically repressed to a basal level in the light (Yoshida et al. 1995).

Expression Patterns of the ntTCTP Gene

Figure 7:
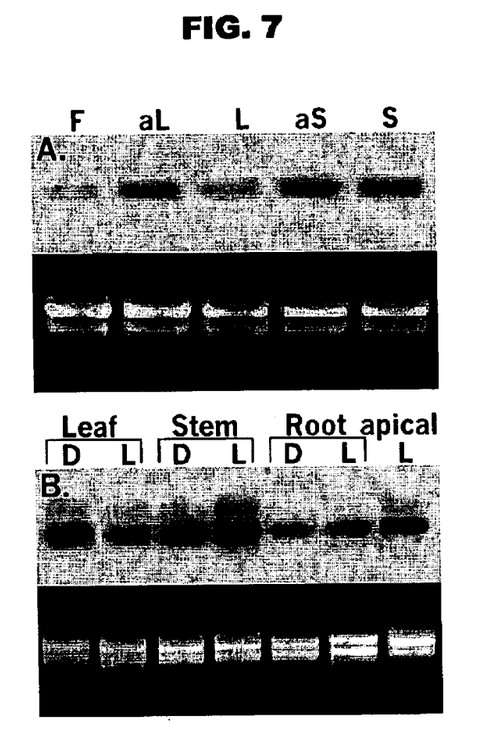
FIG. 7 is Northern blot analyses showing organ-specific expression of the ntTCTP gene and light effect on it. (A) Organ-specific expression. F; floral tissue, L and. S; leaf and stem, aL and aS; apical leaf and stem. (B) Light effect. To examine light effect, plants were grown for 3 weeks in the light and divided into two groups. They were further grown for 7 days either in the dark (D) or in the light (L). The bottom panels of A and B are the ethidium bromide-stained rRNA bands used as internal controls. Each lane contains 10 μg of total RNA.

One prominent, well-established characteristic of plants grown in the dark is the abnormally rapid growth of seedlings via the phytochrome-mediated shade avoidance phenomenon (Mazzella et al. 1997; Botto et al. 1996; Shinomura et al. 1996). Both phytochrome A and Pra3 are highly expressed in the dark-grown plants, but repressed by light. In addition, it has been recently observed that the TCTP expression in the Japanese morning glory plant also exhibits dark-induced expression (sage-Ono et al. 1998). These observations suggest that the TCTP protein has a role in phytochrome-mediated light signal transduction. To investigate the expression patterns of the ntTCTP gene, we conducted a series of RNA gel blot analyses using total RNAs isolated from tobacco plants either grown in the light or in the dark. The transcription level of the ntTCTP gene was at least 5 times higher in the stems than in other plant parts of both the light-grown and dark-grown plants (FIG. 7). However, the light effect Was not as prominent as that observed in the Japanese morning glory plant (sage-Ono et al. 1998). Similar expression profiles were also observed with the pea plant. The reason for this inconsistency is currently unclear, but it may reflect some physiological differences between short-day and long-day plants.

Hormone Effects on the ntTCTP Expression

Figure 8:
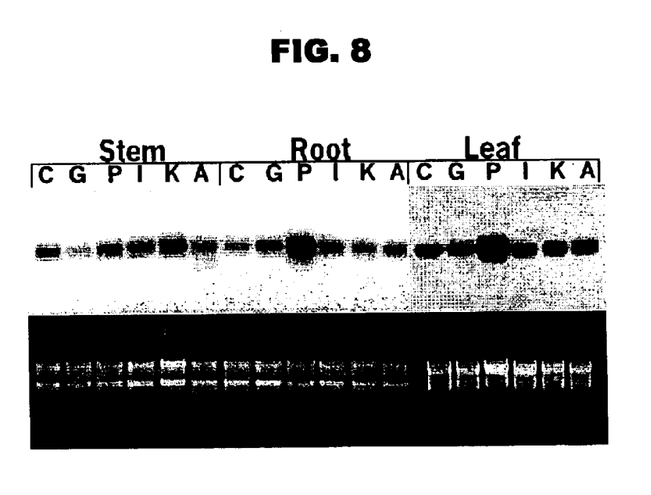

To investigate the effects of plant growth hormones on the ntTCTP expression, tobacco plants were treated with various growth hormones and the transcription levels of the ntTCTP in different plant parts were examined as shown in FIG. 8. Growth hormones did not show any significant effects on the ntTCTP expression in all plant parts tested, although slight induction was observed in stems when treated with IAA and kinetin. However 15% PEG treatment, which mimics the water-deficient condition, markedly induced the ntTCTP transcription by a facot of 7–8 times in leaf and root. The inducible effect in stem was not apparent as that in root and leaf. This suggests that the TCTP has some regulatory role in drought stress by itself or via an interaction with the regulatory mechanism for cell proliferation. It seems that the TCTP is not a direct mediator in light signal transduction but involved in stress signaling. This could explain why the psTCTP gene expression was induced in the root caps when the root tips were damaged (Woo et al. 1997).

Recombinant TCTP Protein

Figure 9:
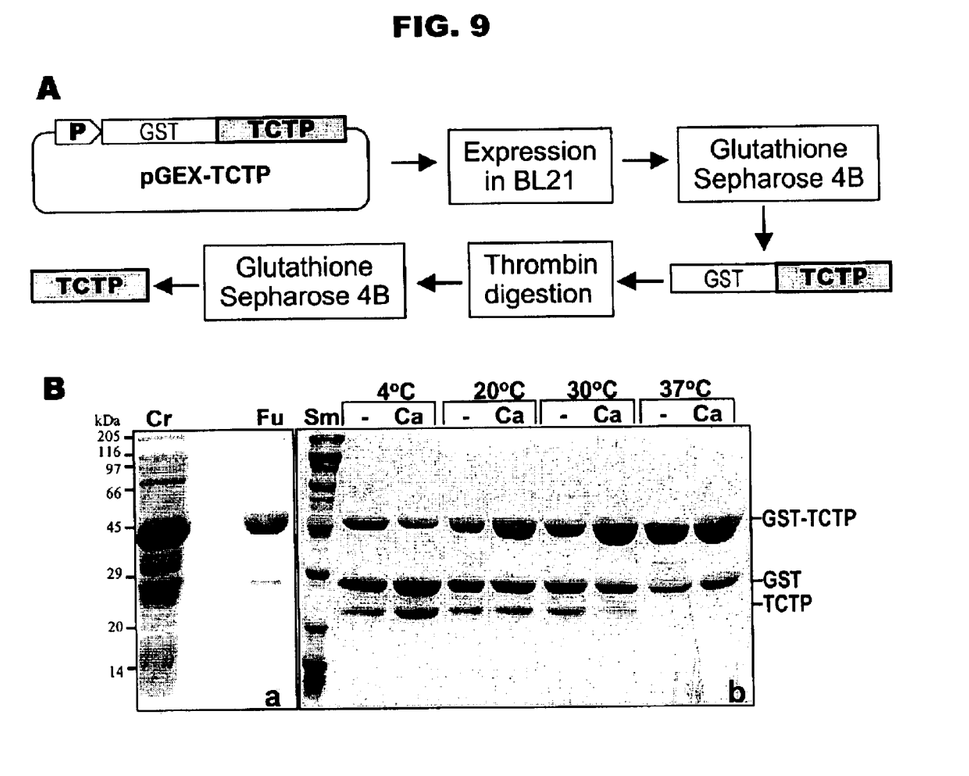
FIG. 9 shows the recombinant ntTCTP protein expressed in E. coli and purified by glutathione-affinity chromatography (Amersham Pharmacia, Piscataway, N.J.). (A) A schematic procedure for the expression and purification of ntTCTP. The Glutathione-S-transferase (GST) was fused to the N-terminus of the ntTCTP, and the fusion protein was expressed in E. coli strain BL21. (B) The ntTCTP preparations analyzed on a 12% SDS-PAGE. The gel was visualized by 0.25% Coomassie Brilliant Blue R250 staining. (a) The GST-TCTP fusion protein (Fu) was first purified from the crude extract (Cr) by glutathione-affinity chromatography. (b) The purified GST-TCTP fusion protein was then subject to thrombin digestion at different temperatures with (Ca) or without (−) 10 $\mu$M $Ca^{2+}$. GST-TCTP; fusion protein, TCTP and GST; TCTP and GST polypeptides after thrombin digestion, respectively. Molecular mass markers (Sm) are indicated in kilodaltons (kDa) on the left.

To study some biochemical properties of the ntTCTP protein, it was overexpressed in *E. coli* recombinant expression system and isolated as a GST fusion in pure form (FIG. 9A). The ntTCTP was efficiently expressed (25–30 mg/liter culture) in *E. coli*, and most of the expressed protein (more than 90%) was recovered in a soluble form (FIG. 9B-a). No detectable aggregation was observed during the purification steps. To examine the heat-stability, the purified GST-ntTCTP fusion was incubated at various temperatures for up to 24 hours in the presence or absence of $Ca^{2+}$ ion. The $Ca^{2+}$ ion was included in the assays because animal TCTP proteins bind $Ca^{2+}$ ion (Sanchez et al. 1997) and $Ca^{2+}$ binding would induce some conformational changes in the TCTP protein. No degradation and aggregation were detected even after 24 hours at 37° C. (FIG. 9B). Calcium ion did not have any visible effect on the heat-stability. However, it affected the proteolytic digestion of the fusion protein with thrombin. The GST-TCTP fusion was very reluctant to thrombin digestion. However, addition of 10 $\mu M$ $Ca^{2+}$ significantly increased the cleavage efficiency especially at lower temperature (FIG. 9B). It seems that $Ca^{2+}$ binding induced some conformational changes in the TCTP domain of the fusion and rendered the junction peptide region more accessible to the thrombin molecule. The recombinant GST-TCTP fusion was also stable in solution with a pH range of 5–9 (data not shown).

What is claimed is:

1. A transgenic plant cell which is transformed with an expresses a gene encoding the translationally controlled tumor protein (TCTP) (SEQ ID NO:2).

2. A transgenic plant cell of claim 1 wherein the cell is from a plant which is a dicot species.

3. A transgenic plant cell of claim 1 wherein the cell is from a plant which is a monocot species.

4. An expression vector comprising SEQ ID NO:1 fused to a GaMV 35S promoter.

* * * * *